United States Patent
Yu et al.

(10) Patent No.: US 8,530,723 B2
(45) Date of Patent: Sep. 10, 2013

(54) **MARKERS ASSOCIATED WITH RESISTANCE TO *APHIS GLYCINES* AND METHODS OF USE THEREFOR**

(75) Inventors: Ju kyung Yu, Northfield, MN (US); Becky Breitinger, Northfield, MN (US); Virgil Sparks, Carroll, IA (US); Harish Gandhi, Huxley, IA (US)

(73) Assignee: Syngenta Participations AG, Basel (CH)

( * ) Notice: Subject to any disclaimer, the term of this patent is extended or adjusted under 35 U.S.C. 154(b) by 497 days.

(21) Appl. No.: 12/757,206

(22) Filed: Apr. 9, 2010

(65) Prior Publication Data

US 2010/0263085 A1 Oct. 14, 2010

Related U.S. Application Data

(60) Provisional application No. 61/168,062, filed on Apr. 9, 2009.

(51) Int. Cl.
*A01H 1/04* (2006.01)
*C12N 15/10* (2006.01)
*C12N 15/29* (2006.01)

(52) U.S. Cl.
USPC ............................ 800/265; 800/267; 800/312

(58) Field of Classification Search
None
See application file for complete search history.

(56) References Cited

U.S. PATENT DOCUMENTS

2006/0015964 A1* 1/2006 Hill et al. ...................... 800/279

* cited by examiner

*Primary Examiner* — David T Fox
*Assistant Examiner* — Jared Shapiro
(74) *Attorney, Agent, or Firm* — Dale Skalla

(57) ABSTRACT

Methods for conveying *Aphis glycines* resistance (RAG) into non-resistant soybean germplasm are provided. In some embodiments, the methods include introgressing RAG into a non-resistant soybean using one or more nucleic acid mark

```
 61  ATTGAAAAGGTATGTCCTTCCCTTGTGTTTGGACAACTTACTATTTARCAACGAACAAAA
     TAACTTTTCCATACAGGAAGGGAACACAAACCTGTTGAATGATAAATYGTTGCTTGCTTTT
                   SEQ ID NO: 4
                   ────────────────────────────────────────────►
121  CTTACATACAAATCTTTAGGCTCCTTATAACCTTGTTATTTGATCAAAATTAAAGTTTYA
     GAATGTATGTTTAGAAATCCGAGGAATATTGGAACAATAAACTAGTTTTAATTTCAAART
181  TTTCAATAATCTACATAATAGAWGTTTACATGTAGATTATCGAGATAAACTTCAATTTTG
     AAAGTTATTAGATGTATTATCTWCAAATGTACATCTAATAGCTCTATTTGAAGTTAAAAC
                      ─────────────────────
                      SEQ ID NOS: 10 and 13
                            ◄────────────
241  GTCGAAAATAAACACCAAATATACTTATAAAATTACATCTAAGTTTTATCCTTCAACAAA
     CAGCTTTTATTTGTGGTTTATATGAATATTTTAATGTAGATTCAAAATAGGAAGTTGTTT
     ───────────
     SEQ ID NO: 5
301  TGACACARGCATTGGGATTCTCTTCCATGCTTGGAGCATAGTAGTKTGTGGTCATGTAGG
     ACTGTGTYCGTAACCCTAAGAGAAGGTACGAACCTCGTATCATCAMACACCAGTACATCC
```

FIGURE 2A

```
 61  AGATAAAGGAAGTATGGTCCATGGACTCCCCAGGAACATCCTCGTGCTTAGAGGGCTTCT
     TCTATTTCCTTCATACCAGGTACCTGAGGGGTCCTTGTAGGAGCACGAATCTCCCGAAGA\

SEQ ID NO: 6
                        ────────────────────────────────────────▶
121  CCTTCCCACCAACCAACCTGGCTGGGTTCCCAACAGCTGTTGTCTGTGGTGGCACATCGA
     GGAAGGGTGGTTGGTTGGACCGACCCAAGGGTTGTCGACAACAGACACCACCGTGTAGCT

181  TTAAAACCACSGAGCCAGCACCAACCTTTGCACCTTCCCCGATCTTAATATTCCCCAGAA
     AATTTTGGTGSCTCGGTCGTGGTTGGAAACGTGGAAGGGCTAGAATTATAAGGGGTCTT
                       ◀────────────────────
     ─────────────          SEQ ID NO: 7
     SEQ ID NOS:
     11 and 14

241  TGGTAGCACCGGCACCAATAAGCACCCCATCCCCAATCTTGGGATGCCGGTCCCCACCAA
     ACCATCGTGGCCGTGGTTATTCGTGGGGTAGGGGTTAGAACCCTACGGCCAGGGGTGGTT
```

FIGURE 2B

```
481   CCAGAGACAAGACTCCGCACTGTTYTCCTAGTWCCCACTTTGTGAGAACTAACCCCATTTCC
      GGTCTGTTCTGAGGCGTGACAARAGGATCAWGGGTGAAACACTCTTGATTGGGGTAAAGG

SEQ ID NO: 8
541   ATTAACTTTTTTTCTTTCTTTCAAAAAATAAAACAAAGAAGGCTTCAAAATTTGTAAAT
      TAATTGAAAAAAAAGAAAGAAAGTTTTTATTTGTTTCTTCCGAAGTTTTAAAACATTTA

SEQ ID NOS: 12 and 15
601   AAATTAAGAGTCTCRTCCTGTGTATGGAATAACATCAATTAGAAGAGCTCAATCACCTAA
      TTTAATTCTCAGAGYAGGACACATACCTTATTGTAGTTAATCTTCTCGAGTTAGTGGATT
                                                    SEQ ID NO: 9

661   ACAAATCTCATTACATTGAGATATTAGTGTTTGACTCGATACCACCCCAGAAAAATAAGG
      TGTTTAGAGTAATGTAACTCTATAATCACAAACTGAGCTATGGTGGGGTCTTTTTATTCC

721   CCTGATTTTTCTGCTAAACGTACACCCCTTAATTACAGAAATGTTTATATCAGAGCAGT
      GGACTAAAAAGACGATTTGCATGTGGGAATTAATGTCTTTACAAATATAGTCTCGTCA
```

FIGURE 2C

```
                    SEQ ID NO: 21
                  SEQ ID NO: 20
1   CCAGTATCACAAACAAGTCATGGGTGACCAAARCAATTGGAGATTTTCCCATGTGTTGTCTTC
    GGTCATAGTGTTTGTTCAGTACCCACTGGTTTYGTTAACCTCTAAAAGGGTACACAACAGAAG
                                                SEQ ID NO: 28

64  AACATGAAACTGTGKAGGCTAACAACTTATCCTCATTTATYTGCAGGATCTGAATATTTAAGA
    TTGTACTTTGACAGMTCCGATTGTTGAATAGGAGTAAATARACGTCCTAGACTTATAAATTCT
```

FIGURE 3A

SEQ ID NOS: 22 AND 23
→
51 ATGTGTTGTCTTCAACATGAAACTGTGKAGGCTAACAACTTATCCTCATTTATYTGCAGGATCTG
TACACAACAGAAGTTGTACTTTGACACMTCCGATTGTTGACACMTCCGATTGTTGAATAGGAGTAAATARACGTCCTAGAC
←
SEQ ID NO: 29

116 AATATTTAAGACTAGCGACACACAGAGGATATAACCAGGGCCAGGTAAATTTTCCCAATAAATACA
TTATAAATTCTGATCGCTGTGTGTCTCCTATATTGGTCCCGTCCATTTAAAAGGGTTATTTATGT

FIGURE 3B

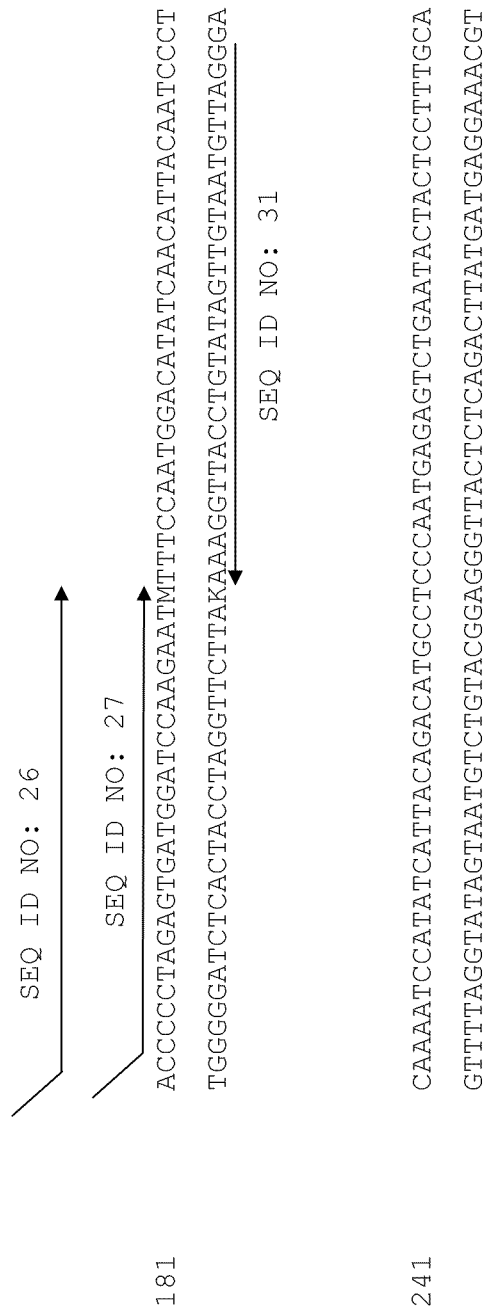

MARKERS ASSOCIATED WITH RESISTANCE TO *APHIS GLYCINES* AND METHODS OF USE THEREFOR

RELATED APPLICATION

This application claims the benefit under Title 35, United States Code, §119(e) of U.S. provisional application 61/168,062 filed Apr. 9, 2009.

TECHNICAL FIELD

The presently disclosed subject matter relates to markers associated with resistance to *Aphis glycines* (RAG) and methods of use therefor. More particularly, the presently disclosed subject matter relates to screening soybean lines for resistance to aphids and for producing soybean lines with improved resistance to aphids, the methods involving genetic marker analysis. The presently disclosed subject matter further includes methods for monitoring the introgression quantitative trait loci (QTL) conferring aphid resistance into elite germplasm in a breeding program.

INCORPORATION BY REFERENCE

PCT International Patent Application Publication Nos. WO 2008/067043, filed Oct. 10, 2006; WO 2006/002162, filed Jun. 21, 2005; WO 2006/125065, filed May 18, 2006; and U.S. patent application Ser. No. 11/158,307 (published as U.S. Patent Application Publication No. 2006/0015964), filed Jun. 21, 2005, are hereby incorporated by reference in their entireties to the extent not inconsistent herewith.

INCORPORATION OF THE SEQUENCE LISTING

A Sequence Listing is contained in the file named "139273_ST25.txt", which is 8 kilobytes (measured in MS-Windows) and was created on Apr. 6, 2009. The Sequence Listing is attached and filed herewith and is incorporated herein by reference.

BACKGROUND

The soybean aphid, *Aphis glycines*, can cause massive damage and over 50% yield loss to soybean crops resulting in significant agricultural losses with widespread consequences for both the food supply and other industries that rely on plant materials. Soybean cultivars currently available commercially in the United States are all susceptible to *Aphis glycines* to some degree, and insecticide applications are currently employed to control the disease. In addition to crop loss, increased use of insecticides to combat aphids decreases farmers' profits and may adversely affect the environment and consumer preferences. Over seven million acres of soybeans in the North Central U.S. were sprayed with insecticide to control soybean aphids in 2003 at an estimated cost of $84-$105 million (Landis et al. NCR-125 Arthropod biological control: state reports for 2003; Li et al., Mol Breeding 19:25-34, 2007).

Soybean aphids directly damage the soybean plant by removing significant amounts of water and nutrients resulting in yellow and wilted leaves. Aphids also excrete honeydew, a sugary sticky substance, on to the leaves and plants. The presence of honeydew often leads to the development of sooty mold, which adversely affects photosynthesis and results in significant yield losses (Gomez et al., Environ Exp Bot 55: 77-86 (2006)). Soybean aphids are also vectors for a number of viruses that can inhibit plant growth, distort leaves, cause mottling of leaves and stem, reduce pod number, and cause seed discoloration. Viruses transmitted via soybean aphid include, soybean mosaic virus, yellow mosaic virus, tobacco etch virus, and tobacco vein mottling virus (Wang et al. Plant Dis 90: 920-926 (2006)). As such, there is a long felt need to reduce the incidence and/or impact of aphids on crop production. Aphid resistant cultivars are needed to reduce insecticide costs and yield losses due to *Aphis glycines*.

There is a need for rapid, cost-efficient method to assay the absence or presence of aphid resistance loci in soybean and there is a need for soybean plants and seeds which exhibit resistance to the soybean aphid.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for conveying resistance to *Aphis glycines* (RAG) into non-resistant soybean germplasm. In some embodiments, the methods comprise introgressing RAG into a non-resistant soybean using one or more nucleic acid markers for marker-assisted breeding among soybean lines to be used in a soybean breeding program, wherein the markers are linked to the Rag1 locus. In some embodiments, the one or more nucleic acid markers are selected from the group consisting of SEQ ID NOs: 1-3, and SEQ ID NOs: 19 and informative fragments thereof. In some embodiments, the marker-assisted breeding comprises single nucleotide polymorphism (SNP) analysis. In some embodiments, the methods further comprise screening an introgressed soybean plant, or a cell or tissue thereof, for RAG.

The presently disclosed subject matter also provides methods for reliably and predictably introgressing *Aphis glycines* resistance (RAG) into non-resistant soybean germplasm. In some embodiments, the methods comprise employing one or more nucleic acid markers for marker-assisted breeding among soybean lines to be used in a soybean breeding program, wherein the nucleic acid markers are selected from the group consisting of SEQ ID NOs: 1-3 and SEQ ID NOs: 19, and informative fragments thereof, and introgressing the resistance into the non-resistant soybean germplasm. In some embodiments, the marker-assisted breeding comprises single nucleotide polymorphism (SNP) analysis. In some embodiments, the methods further comprise screening an introgressed soybean for RAG.

The presently disclosed subject matter also provides methods for producing an inbred soybean plant adapted for conferring, in hybrid combination with a suitable second inbred, resistance to *Aphis glycines* (RAG). In some embodiments, the methods comprise (a) selecting a first donor parental line possessing a desired RAG and having at least one of the resistant loci selected from a locus mapping to Rag1 and mapped by one or more of the markers SEQ ID NOs: 1-3 and SEQ ID NOs: 19; (b) crossing the first donor parent line with a second parental line in hybrid combination to produce a segregating plant population; (c) screening the segregating plant population for identified chromosomal loci of one or more genes associated with the RAG; and (d) selecting plants from the population having the identified chromosomal loci for further screening until a line is obtained which is homozygous for RAG at sufficient loci to give RAG in hybrid combination.

The presently disclosed subject matter also provides methods for selecting an *Aphis glycines* resistant soybean plant. In some embodiments, the methods comprise (a) genotyping one or more soybean plants with respect to one or more single nucleotide polymorphisms (SNPs), wherein the one or more SNPs correspond to one or more molecular markers selected from the group consisting of SEQ ID NOs: 1-3 and SEQ ID NOs: 19, and informative fragments thereof; and (b) selecting a soybean plant that includes at least one resistance allele associated with the SNPs, thereby selecting an *Aphis glycines* resistant soybean plant. In some embodiments, the at least one resistance allele is associated with an allele having an A at nucleotide 203 of SEQ ID NO: 1; a C at position 191 of SEQ ID NO: 2; and/or an A at position 615 of SEQ ID NO: 3; an A at position 33 of SEQ ID NOs: 19; a T at position 78 of SEQ ID NOs: 19; a T at position 104 of SEQ ID NOs: 19; an A at position 208 of SEQ ID NOs: 19.

In some embodiments, the presently disclosed methods comprise (a) isolating one or more nucleic acids from a plurality of soybean plants; (b) detecting in said isolated nucleic acids the presence of one or more marker molecules associated with RAG, wherein said marker molecule is selected from the group consisting of SEQ ID NOs: 1-3 and SEQ ID NOs: 19, informative fragments thereof, and any marker molecule mapped within 1, 2, 3, 4, 5, 6, 7, 8, 9, or 10 centiMorgans or less from said marker molecules; and (c) selecting a soybean plant comprising said one or more marker molecules, thereby selecting an *Aphis glycines* resistant soybean plant. In some embodiments, the at least one resistance allele is associated with an allele having an A at nucleotide 203 of SEQ ID NO: 1; a C at position 191 of SEQ ID NO: 2; and/or an A at position 615 of SEQ ID NO: 3; an A at position 33 of SEQ ID NOs: 19; a T at position 78 of SEQ ID NOs: 19; a T at position 104 of SEQ ID NOs: 19; an A at position 208 of SEQ ID NOs: 19.

The presently disclosed subject matter also provides *Aphis glycines* resistant soybean plants, parts thereof (including but not limited to pollen, ovule, leaf, embryo, root, root tip, anther, flower, fruit, stem, shoot, seed; scion, rootstock, protoplast, and callus), and progeny thereof, selected using the disclosed methods.

Thus, it is an object of the presently disclosed subject matter to provide methods for conveying RAG into non-resistant soybean germplasm.

It is also an object of the presently disclosed subject matter to provide methods for screening and selecting an aphid resistant soybean plant using single nucleotide polymorphism (SNP) technology.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIGS. 2A-2C are a series of depictions of subsequences of SEQ ID NOs: 1-3 (presented in the Figures in double stranded form) and oligonucleotide primer sets that can be employed to distinguish between different alleles at the indicated SNP sites (nucleotide presented in bold type). In FIGS. 2A-2C, arrows pointing left-to-right indicate that the relevant primer has a sequence that would be expected to bind to the reverse-complement of the indicated subsequence/strand, whereas arrows pointing right-to-left indicate that the relevant primer has a sequence that would be expected to bind to the indicated subsequence/depicted strand itself. Solid lines without arrowheads depict the location of primers that can be employed to discriminate between different alleles at the SNP site.

FIGS. 3a-3d and oligonucleotide primer sets that can be employed to distinguish between different alleles at the indicated SNP sites (nucleotide presented in bold type). In FIGS. 3a-3d, arrows pointing left-to-right indicate that the relevant primer has a sequence that would be expected to bind to the reverse-complement of the indicated subsequence/strand, whereas arrows pointing right-to-left indicate that the relevant primer has a sequence that would be expected to bind to the indicated subsequence/depicted strand itself. Solid lines without arrowheads depict the location of primers that can be employed to discriminate between different alleles at the SNP site. FIG. 3a shows the location for SNP at position 33; FIG. 3b shows the location for SNP at position 78; FIG. 3c shows the location for SNP at position 104; and, FIG. 3d shows the location for SNP at position 208.

BRIEF DESCRIPTION OF THE SEQUENCE LISTING

Figure 1:
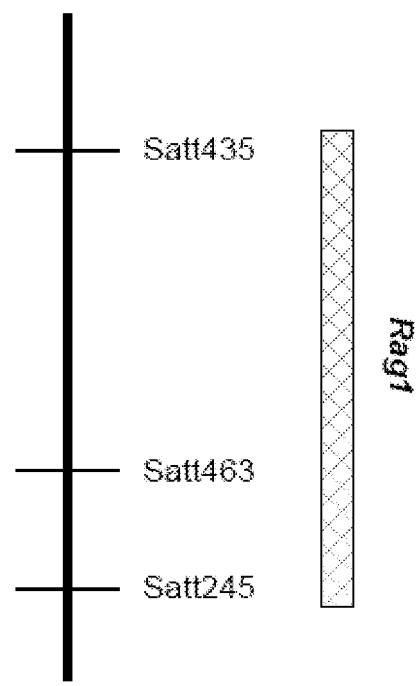
FIG. 1 is a genetic linkage map depicting a portion of linkage group M and showing relative positions of various markers linked to Rag1.
Figure 3C:
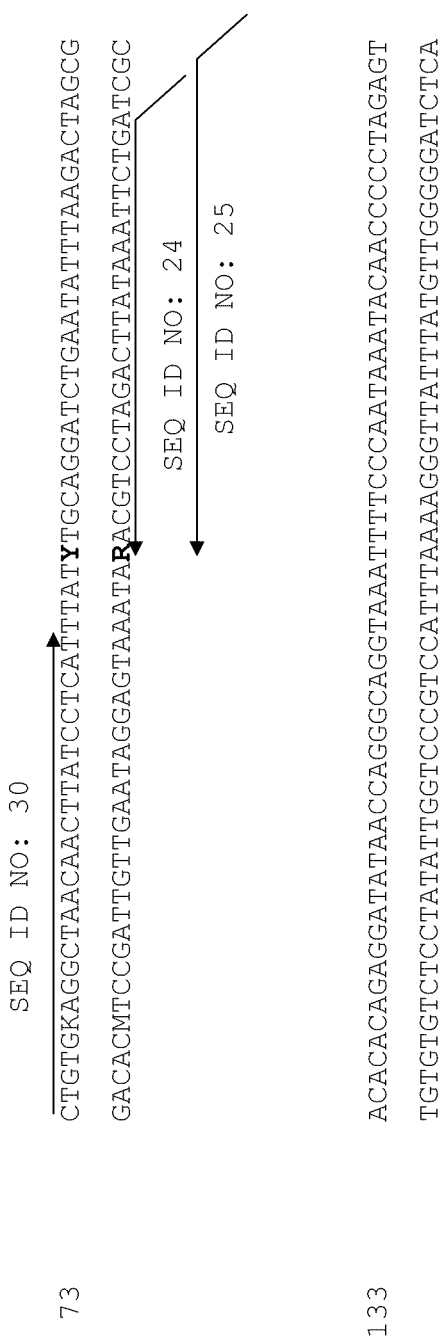

SEQ ID NOs: 1-3 and SEQ ID NOs: 19 are nucleotide sequences of various subsequences of the soybean genome that comprise single nucleotide polymorphisms, (SNPs) identified as being associated with Rag1 genes on chromosome Gm 07 as set forth in Table 1.

TABLE 1

SEQ ID NOs., SNP Codes, and Map Positions for Markers

| SEQ ID NO. | Linkage Group | cM position |
|---|---|---|
| 1 | M | 38.048 |
| 2 | M | 39.1 |
| 3 | M | 47.4 |
| 19 | M | 41.4 |
| 19 | M | 41.4 |
| 19 | M | 41.4 |
| 19 | M | 41.4 |

SEQ ID NOs: 4-15 are nucleotide sequences of various oligonucleotide primers that can be used to screen *Glycine max* nucleic acids for the presence of one or more of SNPs identified as being associated with Rag1 genes as set forth in Table 2.

SEQ ID NOs: 4-9 are nucleotide sequences of oligonucleotide primers that can be employed to amplify and/or otherwise assay a subsequence of the soybean genome that is associated with the Rag1 locus. The locations of these primers are depicted in FIGS. 2A-2C.

SEQ ID NOs: 10-12 are nucleotide sequences of VIC oligonucleotide probes. The locations of these probes are depicted in FIGS. 2A-2C.

SEQ ID NOs: 13-15 are nucleotide sequences of FAM oligonucleotide probes. The locations of these probes are depicted in FIGS. 2A-2C.

TABLE 2

SEQ ID NOs., SNP Codes, and Related Primers and Markers

| SEQ ID NO. | Resistance Allele | Forward Primer SEQ ID NO. | Reverse Primer SEQ ID NO. | VIC Probe SEQ ID NO. | FAM Probe SEQ ID NO. |
|---|---|---|---|---|---|
| 1 | A at nucleotide 203 | 4 | 5 | 10 | 13 |
| 2 | C at nucleotide 191 | 6 | 7 | 11 | 14 |
| 3 | A at nucleotide 615 | 8 | 9 | 12 | 15 |

| SEQ ID NO. | Resistance Allele | Forward 1 Primer SEQ ID NO. | Forward 2 Primer SEQ ID NO. | Reverse Primer SEQ ID NO. |
|---|---|---|---|---|
| 19 | A at nucleotide 33 | 20 | 21 | 28 |
| 19 | T at nucleotide 78 | 22 | 23 | 29 |
| 19 | T at nucleotide 104 | 24 | 25 | 30 |
| 19 | A at nucleotide 208 | 26 | 27 | 31 |

SEQ ID NO: 16 corresponds to nucleotides 5899120-5899617 of the assembly of the soybean (*Glycine max*) genomic sequence present in the Phytozyme Database, which is 99.4% identical to nucleotides 1-498 of SEQ ID NO: 1.

SEQ ID NO: 17 corresponds to nucleotides 5227471-5227115 of the assembly of the soybean (*Glycine max*) genomic sequence present in the Phytozyme Database, which is 98.9% identical to nucleotides 360-1 of SEQ ID NO: 2.

SEQ ID NO: 18 corresponds to nucleotides 8426497-8427199 of the assembly of the soybean (*Glycine max*) genomic sequence present in the Phytozyme Database, which is 99.4% identical to nucleotides 35-739 of SEQ ID NO: 3.

SEQ ID NO. 19: is 97.3% identical (567/593) to nucleotides 6404613 to 6405186 of what is identified as "Gm07" (*Glycine max* Chromosome 7) in the Phytozyme Database.

DETAILED DESCRIPTION

The presently) disclosed subject matter relates at least in part to the identification of several SNPs that are not previously associated with RAG in *Glycine* sp. Thus, provided herein are methods of conveying RAG into non-resistant soybean germplasm, which employ one or more of the identified SNPs in various approaches.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the articles "a", "an", and "the" refer to "one or more" when used in this application, including in the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates in some embodiments to SNPs, it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, a trait, locus, QTL, SNP, gene, marker, phenotype, etc. is "associated with resistance" if the presence or absence of the trait, locus, QTL, SNP, gene, marker, phenotype, etc., influences an extent or degree of resistance (e.g., RAG). In some embodiments, an allele associated with RAG comprises an allele having an A at nucleotide 203 of SEQ ID NO: 1; a C at position 191 of SEQ ID NO: 2; and/or an A at position 615 of SEQ ID NO: 3; an A at position 33 of SEQ ID NOs: 19; a Tat position 78 of SEQ ID NOs: 19; a Tat position 104 of SEQ ID NOs: 19; an A at position 208 of SEQ ID NOs: 19.

As used herein, the term "backcross", and grammatical variants thereof, refers to a process in which a breeder crosses a progeny individual back to one of its parents, for example, a first generation hybrid F1 with one of the parental genotypes of the F1 hybrid. In some embodiments, a backcross is performed repeatedly, with a progeny individual of one backcross being itself backcrossed to the same parental genotype.

As used herein, the term "F2:3 population" refers to F3 plant families derived from F2 plants.

The term "chromosome" is used herein in its art-recognized meaning of the self-replicating genetic structure in the cellular nucleus containing the cellular DNA and bearing in its nucleotide sequence the linear array of genes.

As used herein, the terms "cultivar" and "variety" refer to a group of similar plants that by structural or genetic features and/or performance can be distinguished from other varieties within the same species.

As used herein, the term "gene" refers to a hereditary unit including a sequence of DNA that occupies a specific location on a chromosome and that contains the genetic instruction for a particular characteristics or trait in an organism.

As used herein, the term "heterozygous" refers to a genetic condition existing when different alleles reside at corresponding loci on homologous chromosomes.

As used herein, the term "homozygous" refers to a genetic condition existing when identical alleles reside at corresponding loci on homologous chromosomes.

As used herein, the term "hybrid" in the context of nucleic acids refers to a double-stranded nucleic acid molecule, or duplex, formed by hydrogen bonding between complementary nucleotide bases. The terms "hybridize" or "anneal" refer to the process by which single strands of nucleic acid sequences form double-helical segments through hydrogen bonding between complementary bases.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or variety or line.

As used herein, the phrase "informative fragment" refers to a nucleic acid molecule and/or its nucleotide sequence that allows for the proper identification as to which allele (e.g., a SNP) of an allele pair a SNP the nucleic acid molecule and/or the nucleotide sequence corresponds. For example, whereas the SNP that corresponds to SEQ ID NO: 1 relates to an "A" or a "T" at position 203, an "informative fragment" of SEQ ID NO: 1 would be any sequence that comprises position 203 of SEQ ID NO: 1, thereby allowing the nucleotide that is present in that position to be determined.

As used herein, the terms "introgression", "introgressed", and "introgressing" refer to both a natural and artificial process whereby genomic regions of one species, variety, or cultivar are moved into the genome of another species, variety, or cultivar, by crossing those species. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

In some embodiments, "linkage" implies physical proximity on a chromosome. Thus, two loci are linked if they are within 50 centiMorgans (cM) of each other. As such, two loci are linked if they are in some embodiments less than 10, in some embodiments 9, in some embodiments 8, in some embodiments 7, in some embodiments 6, in some embodiments 5, in some embodiments 4, in some embodiments 3, in some embodiments 2, and in some embodiments 1 centiMorgans (cM) of each other. For example, a SNP can be linked to a marker if it is in some embodiments within 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that linkage group can also be defined as corresponding to a region of (i.e., less than the entirety) of a given chromosome.

As used herein, the term "locus" refers to a position that a given gene or a regulatory sequence occupies on a chromosome of a given species.

As used herein, the term "marker" refers to an identifiable position on a chromosome the inheritance of which can be monitored. In some embodiments, a marker comprises a known or detectable nucleic acid sequence.

In some embodiments, a marker corresponds to an amplification product generated by amplifying a *Glycine* sp. nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Glycine* sp. genomic DNA with a particular set of primers. In some embodiments, the amplifying is by PCR, and the primers are PCR primers that are designed to hybridize to opposite strands of the *Glycine* sp. genomic DNA in order to amplify a *Glycine* sp. genomic DNA sequence present between the sequences to which the PCR primers hybridize in the *Glycine* sp. genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the *Glycine* sp. genomic DNA located between the primers, and the complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer, the sequence located between the forward and reverse primers of the top strand of the genomic fragment, and the complement of the reverse primer. Accordingly, a marker that "corresponds to" an amplified fragment is a marker that has the same sequence of one of the strands of the amplified fragment.

As used herein, the term "soybean" refers to a plant, or a part thereof, of the genus *Glycine* including, but not limited to *Glycine max*.

As used herein, the phrase "soybean-specific DNA sequence" refers to a polynucleotide sequence having a nucleotide sequence homology of in some embodiments more than 50%, in some embodiments more than 55%, in some embodiments more than 60%, in some embodiments more than 65%, in some embodiments more than 70%, in some embodiments more than 75%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the genus *Glycine* that shows the greatest similarity to it, in some embodiments in the case of markers for Rag1, the part of the DNA sequence of a soybean flanking and/or including any of the Rag1 gene sequence.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which define a specific genetic and chromosomal location. A molecular marker "linked to" or "associated with" a Rag gene as defined herein can thus refer to SNPs, insertion mutations, as well as more usual AFLP markers or any other type of marker used in the field.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology can be determined by comparing two optimally aligned sequences over a comparison window, wherein the portion of the polynucleotide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalX (Chenna et al., 2003) programs, both available on the internet. Other suitable programs include, but are not limited to, GAP, BestFit, PlotSimilarity, and FASTA, which are part of the Accelrys GCG Package available from Accelrys, Inc. of San Diego, Calif., United States of America.

As used herein, the term "offspring" plant refers to any plant resulting as progeny from a vegetative or sexual reproduction from one or more parent plants or descendants thereof. For instance an offspring plant can be obtained by cloning or selfing of a parent plant or by crossing two parent plants and can include selfings as well as the F1 or F2 or still further generations. An F1 is a first-generation offspring produced from parents at least one of which is used for the first time as donor of a trait, while offspring of second generation (F2) or subsequent generations (F3, F4, and the like.) are specimens produced from selfings (self pollinating) of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the term "phenotype" refers to a detectable characteristic of a cell or organism, which characteristics are at least partially a manifestation of gene expression.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" refers to a genetically heterogeneous collection of plants sharing a common genetic derivation.

As used herein, the term "primer" refers to an oligonucleotide which is capable of annealing to a nucleic acid target allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH).

The primer (in some embodiments an extension primer and in some embodiments an amplification primer) is in some embodiments single stranded for maximum efficiency in extension and/or amplification. In some embodiments, the primer is an oligodeoxyribonucleotide.

A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer.

In the context of an amplification primer, these are typically provided as a pair of bi-directional primers consisting of one forward and one reverse primer as commonly used in the art of DNA amplification such as in PCR amplification.

In the case of allele specific PCR, there will be 2 primers in one direction, corresponding to each allele of a SNP, and one common primer in the opposite orientation.

As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or include nucleotides which allow a typical base pairing.

Primers can be prepared by any suitable method. Methods for preparing oligonucleotides of specific sequence are known in the art, and include, for example, cloning, and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties, for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotide triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, $E.$ $coli$ DNA polymerase I or its Klenow fragment, T4 DNA polymerase, and Taq DNA polymerase, as well as various modified versions thereof. The reaction conditions for catalyzing DNA synthesis with these DNA polymerases are known in the art. The products of the synthesis are duplex molecules consisting of the template strands and the primer extension strands, which include the target sequence. These products, in turn, can serve as a template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

Continuing, the term "probe" refers to a single-stranded oligonucleotide sequence that will form a hydrogen-bonded duplex with a complementary sequence in a target nucleic acid sequence analyte or its cDNA derivative.

As used herein, the term "Rag1" refers to loci that have been associated with RAG. For the purposes of the instant disclosure, these loci are said to be present on the Glycine linkage group M and linked to the markers depicted in FIG. 1, the sequence data and Table 1.

As used herein, the term "quantitative trait locus" (QTL; plural quantitative trait loci; QTLs) refers to a genetic locus (or loci) that control to some degree a numerically representable trait that, in some embodiments, is continuously distributed. As such, the term QTL is used herein in its art-recognized meaning to refer to a chromosomal region containing alleles (e.g., in the form of genes or regulatory sequences) associated with the expression of a quantitative phenotypic trait. Thus, a QTL "associated with" RAG refers to one or more regions located on one or more chromosomes and/or in one or more linkage groups that includes at least one gene the expression of which influences a level of resistance and/or at least one regulatory region that controls the expression of one or more genes involved in RAG. A QTL can comprise multiple genes or other genetic factors even within a contiguous genomic region or linkage group. QTLs can be defined by indicating their genetic location in the genome of a specific *Glycine* sp. accession using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the end-point markers is indicative of the size of the QTL.

As used herein, the term "recombination" refers to an exchange (a "crossover") of DNA fragments between two DNA molecules or chromatids of paired chromosomes over in a region of similar or identical nucleotide sequences. A "recombination event" is herein understood to refer to a meiotic crossover.

As used herein, the term "regenerate", and grammatical variants thereof, refers to the production of a plant from tissue culture.

As used herein, aphid resistance refers to preventing or inhibiting the ability of aphids to cause damage, such as reducing feeding, delaying growth and developing, reducing fecundity and the like, to a host plant.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Longer sequences hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For selective or specific hybridization, a positive signal is in some embodiments at least two times background, in some embodiments at least three times background, in some embodiments at least five times background, and in some embodiments at least ten times background hybridization. Exemplary stringent hybridization conditions include: 50% formamide, 5×SSC, and 1% SDS, incubating at 42° C.; or 5×SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al. 1999).

As used herein, the soybean aphid, *Aphis glycines*, refers to an aphid that feeds on soybean. However, any aphid that is found on and feeds on a soybean plant, such as the bean aphid, *Aphis fabae*, is a target for aphid resistance in soybean and is within the scope of the presently disclosed subject matter.

II. General Considerations

The soybean aphid, native to Asia, was first found in the Midwestern United States in 2000 (Hartman et al., 2001). It rapidly spread throughout North America caused millions of dollars in economic losses (Hill et al. 2006). Resistance was discovered and established in three ancestors of North American genotypes: 'Dowling', 'Jackson', and PI 71506 by Hill et al. (2004). Studies of the inheritance of resistance to the soybean aphid in the Dowling cultivar indicated that a single dominant gene, Rag1, controlled resistance in Dowling (Hill et al. 2006).

Rag1 has been mapped to linkage group (LG) M with flanking SSR markers Satt435, Satt463, and Satt245. Two F2:3 populations (Dowling×Loda and Dowling×Willians82) were created and analyzed to map the resistant Rag1 gene. The populations were genotyped by SSR markers to map the gene and bulk segregant analysis was applied to identify candidate SSR markers. Rag1 was mapped between Satt435 and Satt463 in one population and between Satt435 and Satt245 in the other (Li et al. 2007 Mol Breeding 19:25-34).

Rag1 has been identified as having a strong antibiosis-type aphid resistance (Hill et al. 2004; 2006). Resistance conferred by Rag1 can be race-specific and is not effective against the aphid biotype from Ohio (Kim et al. 2008; Mian et al. 2008a), although this lack of effectiveness is in dispute by some scientists.

The presently disclosed subject matter provides in some embodiments soybean varieties that are resistant to *Aphis glycines*, for example PI567543C or PI548663, methods for identifying soybean plants that carry desirable resistance genes, and methods for introducing such desirable resistance genes into soybeans.

III. Plant Breeding

A purpose of breeding programs in agriculture and horticulture is to enhance the performances of plants by improving their genetic composition. In essence, this improvement accrues by increasing the frequency of the most favorable alleles for the genes influencing the performance characteristics of interest. Wild plant lines provide a rich resource of genetic and phenotypic variation. Traditionally, agricultural or horticultural practice makes use of this variation by selecting a wild plant line or its offspring for having desired genotypic or potential phenotypic properties, crossing it with a line having additional desired genotypic or potential phenotypic properties and selecting from among the offspring plants those that exhibit the desired genotypic or potential phenotypic properties (or an increased frequency thereof).

A growing understanding and utilization of the laws of Mendelian inheritance in combination with molecular genetic tools have in the past century facilitated this selection process. For example, methods for selecting plants for having desired genotypic or potential phenotypic properties have become available based on testing the plant for the presence of a marker (e.g., a SNP) and/or a quantitative trait locus (QTL); i.e., for the presence of a chromosomal region containing alleles associated with the expression of a continuously distributed (quantitative) phenotypic trait.

One of the major problems in breeding programs of cultivated plants is the existence of negative genetic correlation between separate traits. This is for example the case with the negative genetic correlation between reproductive capacity and production in various disease-resistant plant lines. Understanding emerges to show that introgressions of DNA from the genome of one plant line into another can interfere with and/or otherwise negatively affect the expression of basic reproductive traits. Likewise, attempts to introgress resistance-conferring gene sequences from one plant into another can remove resistance traits already present in the recipient line.

Knowledge of the inheritance of various traits allows for the selection of lines homozygous for a locus associated with disease resistance. Use of the knowledge of the genetic origin and location of a desired trait in a breeding program can increase the accuracy of the predicted breeding outcome and can enhance the rate of selection compared to conventional breeding programs. For instance, the fact that the genetic basis of a desired trait is heritably linked to another trait can help to increase uniformity for those two traits among the offspring since a parent homozygous for the desired alleles will pass them to most if not all offspring, resulting in a reduced segregation in the offspring.

The presently disclosed subject matter provides for better models for marker-assisted breeding (MAB). The presently disclosed subject matter therefore relates to methods of plant breeding and to methods to select plants, in particular soybean plants, particularly cultivated soybean plants as breeder plants for use in breeding programs, or cultivated soybean plants for having desired genotypic or potential phenotypic properties, in particular those properties related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus *Glycine* exhibiting resistance towards RAG comprising detecting in the plant the presence of one or more resistance alleles as defined herein. In an exemplary embodiment of the presently disclosed methods for selecting such a plant, the method comprises providing a sample of genomic DNA from a soybean plant; and (b) detecting in the sample of genomic DNA at least one molecular marker associated with RAG. In some embodiments, the detecting can comprise detecting one or more SNPs that are associated with resistance to RAG.

The providing of a sample of genomic DNA from a soybean plant can be performed by standard DNA isolation methods well known in the art.

The detecting of a molecular marker can in some embodiments comprise the use of one or more sets of primer pairs that can be used to produce one or more amplification products that are suitable markers for one of the SNPs. Such a set of primers can comprise, in some embodiments, nucleotide sequences as set forth in SEQ ID NOs: 4-9; SEQ ID NOs: 20-31.

In some embodiments, the detecting of a molecular marker can comprise the use of a nucleic acid probe having a base sequence that is substantially complementary to the nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a molecular marker is designed to discriminate whether a particular allele of a SNP is present or absent in a particular plant.

The presently disclosed methods can also include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length as based on a similar reaction with the same primers with the DNA from the plant in which the marker was first detected or the nucleic acid sequence that corresponds (has a homology of in some embodiments more than 80%, in some embodiments more than 90%, in some embodiments more than 95%, in some embodiments more than 97%, and in some embodiments more than 99%) to the expected sequence as based on the sequence of the marker associated with that SNP in the plant in which the marker was first detected. Upon a review of the instant disclosure, one of ordinary skill in the art would appreciate that markers (e.g., SNP alleles) that are absent in resistant plants, while they were present in the susceptible parent(s) (so-called trans-markers), can also be useful in assays for detecting resistance among offspring plants, although testing the absence of a marker to detect the presence of a specific trait is not optimal.

The detecting of an amplified DNA fragment having the predicted length or the predicted nucleic acid sequence can be performed by any of a number or techniques, including but not limited to standard gel-electrophoresis techniques or by using automated DNA-sequencers. The methods are not described here in detail as they are well known to the skilled person, although exemplary approaches are set forth in the EXAMPLES.

IV. Molecular Markers and SNPs

Molecular markers are used for the visualization of differences in nucleic acid sequences. This visualization can be due to DNA-DNA hybridization techniques after digestion with a restriction enzyme (RFLP) and/or due to techniques using the polymerase chain reaction (e.g., STS, SSR/microsatellites, AFLP, and the like.). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994.

The recombination frequencies of molecular markers on different chromosomes and/or in different linkage groups are generally 50%. Between molecular markers located on the same chromosome or in the same linkage group, the recombination frequency generally depends on the distance between the markers. A low recombination frequency corresponds to a low genetic distance between markers on a chromosome. Comparing all recombination frequencies results in the most logical order of the molecular markers on the chromosomes or in the linkage groups. This most logical order can be depicted in a linkage map (Paterson, 1996). A group of adjacent or contiguous markers on the linkage map that is associated with an increased level of resistance to a disease; e.g., to a reduced incidence of acquiring the disease upon infectious contact with the disease agent and/or a reduced lesion growth rate upon establishment of infection, can provide the position of a locus associated with resistance to that disease.

The markers disclosed herein can be used is various aspects of the presently disclosed subject matter as set forth hereinbelow. Aspects of the presently disclosed subject matter are not to be limited to the use of the markers identified herein, however. It is stressed that the aspects can also make use of markers not explicitly disclosed herein or even yet to be identified. Other than the genetic unit "gene", on which the phenotypic expression depends on a large number of factors that cannot be predicted, the genetic unit "QTL" denotes a region of the genome that is directly related to a phenotypic quantifiable trait.

The markers provided by the presently disclosed subject matter can be used for detecting the presence of one or more RAG alleles of the presently disclosed subject matter in a suspected *Aphis glycines* resistant soybean plant, and can therefore be used in methods involving marker-assisted breeding and selection of *Aphis glycines* resistant soybean plants. In some embodiments, detecting the presence of a particular allele of a SNP of the presently disclosed subject matter is performed with at least one of the markers for the resistance loci defined herein. The presently disclosed subject matter therefore relates in another aspect to a method for detecting the presence of a particular allele associated with RAG, comprising detecting the presence of a nucleic acid sequence of the SNP in a suspected *Aphis glycines* resistant soybean plant, which presence can be detected by the use of the disclosed markers and oligonucleotides.

The nucleotide sequence of a SNP of the presently disclosed subject matter can for instance be resolved by determining the nucleotide sequence of one or more markers associated with the SNP and designing internal primers for the marker sequences that can be used to determine which allele of the SNP is present in the plant. For instance, the nucleotide sequence of the SNPs disclosed herein can be obtained by, for example, by dideoxy chain termination sequencing methods, which are well known in the art.

In embodiments of such methods for detecting the presence of a SNP in a suspected *Aphis glycines* resistant soybean plant, the method can also comprise providing a oligonucleotide or polynucleotide capable of hybridizing under stringent hybridization conditions to a particular nucleic acid sequence of a SNP, in some embodiments selected from the SNPs disclosed herein, contacting the oligonucleotide or polynucleotide with genomic nucleic acid (or a fragment thereof, including, but not limited to a restriction fragment thereof) of a suspected *Aphis glycines* resistant soybean plant, and determining the presence of specific hybridization of the oligonucleotide or polynucleotide to the genomic nucleic acid (or the fragment thereof).

In some embodiments, the method is performed on a nucleic acid sample obtained from the suspected *Aphis glycines* resistant soybean plant, although in situ hybridization methods can also be employed. Alternatively, one of ordinary skill in the art can design specific hybridization probes or oligonucleotides capable of hybridizing under stringent hybridization conditions to the nucleic acid sequence of the allele associated with RAG and can use such hybridization probes in methods for detecting the presence of a SNP allele disclosed herein in a suspected *Aphis glycines* resistant soybean plant.

V. Production of *Aphis glycines* Resistant Soybean Plants by Transgenic Methods According to another aspect of the presently disclosed subject matter, a nucleic acid (in some embodiments a DNA) sequence comprising one or more of SEQ ID NOs: 1-3, SEQ ID NO: 19, or resistance-conferring parts thereof, can be used for the production of a resistant soybean plant of the presently disclosed subject matter. In this aspect, the presently disclosed subject matter provides for the use of SNPs as defined herein or resistance-conferring parts thereof, for producing a resistant soybean plant, which use involves the introduction of a nucleic acid sequence comprising the resistance-associated allele of the SNP into a suitable recipient plant.

Once identified in a suitable donor plant, such as PI567543C or PI548663 which is even a better source of Rag1, the nucleic acid sequence that comprises an *Aphis glycines* resistance allele can be transferred to a suitable recipient plant by any method available. For instance, the nucleic acid sequence can be transferred by crossing an *Aphis glycines* resistant donor plant with a susceptible recipient plant (i.e., by introgression), by transformation, by protoplast fusion, by a doubled haploid technique, by embryo rescue, or by any other nucleic acid transfer system, optionally followed by selection of offspring plants comprising one or more of the presently disclosed *Aphis glycines* resistance alleles. For transgenic methods of transfer, a nucleic acid sequence comprising an *Aphis glycines* resistance allele can be isolated from the donor plant using methods known in the art, and the thus isolated nucleic acid sequence can be transferred to the recipient plant by transgenic methods, for instance by means of a vector, in a gamete, or in any other suitable transfer element, such as a ballistic particle coated with the nucleic acid sequence.

Plant transformation generally involves the construction of an expression vector that will function in plant cells. In the presently disclosed subject matter, such a vector comprises a nucleic acid sequence that comprises an allele associated with RAG, which vector can comprise an *Aphis glycines* resistance-conferring gene that is under control of or operatively linked to a regulatory element, such as a promoter. The expression vector can contain one or more such operably linked gene/regulatory element combinations, provided that at least one of the genes contained in the combinations encodes *Aphis glycines* resistance. The vector(s) can be in the form of a plasmid, and can be used, alone or in combination with other plasmids, to provide transgenic plants that are resistant to *Aphis glycines*, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

One method for introducing an expression vector into a plant is based on the natural transformation system of *Agrobacterium* (see e.g., Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g., Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer are provided for example by Gruber & Crosby, 1993, Moloney et al., 1989, and U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber & Crosby, 1993. General methods of culturing plant tissues are provided for example by Miki et al., 1993 and by Phillips et al., 1988. A reference handbook for molecular cloning techniques and suitable expression vectors is Sambrook & Russell, 2001.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (see e.g., Sanford et al., 1987; Klein et al., 1988; Sanford, 1988; Sanford, 1990; Klein et al., 1992; Sanford et al., 1993). Another method for introducing DNA to plants is via the sonication of target cells (see Zhang et al., 1991). Alternatively, liposome or spheroplast fusion can be used to introduce expression vectors into plants (see e.g., Deshayes et al., 1985 and Christou et al., 1987). Direct uptake of DNA into protoplasts using $CaCl_2$ precipitation, polyvinyl alcohol, or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Other well known techniques such as the use of BACs, wherein parts of the soybean genome are introduced into bacterial artificial chromosomes (BACs), i.e., vectors used to clone DNA fragments (100- to 300-kb insert size; average, 150 kb) in *Escherichia coli* cells, based on a naturally occurring F-factor plasmid found in the bacterium *E. coli*. (Zhao & Stodolsky, 2004) can be employed for example in combination with the BIBAC system (Hamilton, 1997) to produce transgenic plants.

Following transformation of soybean target tissues, expression of the above described selectable marker genes allows for preferential selection of transformed cells, tissues and/or plants, using standard regeneration and selection methods.

VI. Production of *Aphis glycines* Resistant Soybean Plants by Non-Transgenic Methods In some embodiments for producing an *Aphis glycines* resistant soybean plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, which can even be obtained with plant species that cannot be interbred in nature, is tissue cultured into a hybrid plant exhibiting the desirable combination of traits. More specifically, a first protoplast can be obtained from a soybean plant or other plant line that exhibits resistance to infestation by *Aphis glycines*. A second protoplast can be obtained from a second soybean or other plant variety, preferably a soybean line that comprises commercially valuable characteristics, such as, but not limited to disease resistance, insect resistance, valuable nutritional characteristics, and the like. The protoplasts are then fused using traditional protoplast fusion procedures, which are known in the art.

Alternatively, embryo rescue can be employed in the transfer of a nucleic acid comprising one or more *Aphis glycines* resistance loci as described herein from a donor plant to a recipient plant. Embryo rescue can be used as a procedure to isolate embryos from crosses wherein plants fail to produce viable seed. In this process, the fertilized ovary or immature seed of a plant is tissue cultured to create new plants (Pierik, 1999).

The presently disclosed subject matter also relates to methods for producing an *Aphis glycines* resistant soybean plant comprising performing a method for detecting the presence of an allele associated with resistance to *Aphis glycines* in a donor soybean plant according to the presently disclosed subject matter as described above, and transferring a nucleic acid sequence comprising at least one allele thus detected, or a RAG-conferring part thereof, from the donor plant to an *Aphis glycines-susceptible* recipient soybean plant. The transfer of the nucleic acid sequence can be performed by any of the methods previously described herein.

An exemplary embodiment of such a method comprises the transfer by introgression of the nucleic acid sequence from an *Aphis glycines* resistant donor soybean plant into an *Aphis glycines*-susceptible recipient soybean plant by crossing the plants. This transfer can thus suitably be accomplished by using traditional breeding techniques. *Aphis glycines* resistance loci are introgressed in some embodiments into commercial soybean varieties using marker-assisted selection (MAS) or marker-assisted breeding (MAB). MAS and MAB involve the use of one or more of the molecular markers for the identification and selection of those offspring plants that contain one or more of the genes that encode for the desired trait. In the context of the presently disclosed subject matter, such identification and selection can be based on selection of SNP alleles of the presently disclosed subject matter or markers associated therewith. MAB can also be used to develop near-isogenic lines (NIL) harboring the gene of interest, allowing a more detailed study of each gene effect. MAB is also an effective method for development of backcross inbred line populations (see e.g., Nesbitt & Tanksley, 2001; van Berloo et al., 2001). Soybean plants developed according to these embodiments can advantageously derive a majority of their traits from the recipient plant, and derive RAG from the donor plant.

As discussed hereinabove, traditional breeding techniques can be used to introgress a nucleic acid sequence encoding RAG into an *Aphis glycines*-susceptible recipient soybean plant. In some embodiments, a donor soybean plant that exhibits resistance to *Aphis glycines* and comprising a nucleic acid sequence encoding RAG is crossed with an *Aphis glycines*-susceptible recipient soybean plant that in some embodiments exhibits commercially desirable characteristics, such as, but not limited to, disease resistance, insect resistance, valuable nutritional characteristics, and the like. The resulting plant population (representing the F1 hybrids) is then self-pollinated and allowed to set seeds (F2 seeds). The F2 plants grown from the F2 seeds are then screened for resistance to *Aphis glycines*. The population can be screened in a number of different ways.

First, the population can be screened using a traditional disease screen. Such disease screens are known in the art. In some embodiments, a quantitative bioassay is used. Second, marker-assisted breeding can be performed using one or more of the herein-described molecular markers to identify those progeny that comprise a nucleic acid sequence encoding for RAG. Other methods, referred to hereinabove by methods for detecting the presence of an allele associated with RAG, can be used. Also, marker-assisted breeding can be used to confirm the results obtained from the quantitative bioassays, and therefore, several methods can also be used in combination.

*Aphis glycines* resistant soybean plant lines can be developed using the techniques of recurrent selection and backcrossing, selfing, or any other technique used to make varieties or hybrids. In a method of recurrent selection and backcrossing, RAG can be introgressed into a target recipient plant (the recurrent parent) by crossing the recurrent parent with a first donor plant, which differs from the recurrent parent and is referred to herein as the "non-recurrent parent". The recurrent parent is a plant that is non-resistant or has a low level of resistance to *Aphis glycines* and possesses commercially desirable characteristics, such as, but not limited to disease resistance, (additional) insect resistance, valuable nutritional characteristics, and the like. In some embodiments, the non-recurrent parent exhibits RAG and comprises a nucleic acid sequence that encodes RAG. The non-recurrent parent can be any plant variety or inbred line that is cross-fertile with the recurrent parent.

The progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, marker-assisted breeding (MAB) can be performed using one or more of the hereinbefore described molecular markers, hybridization probes, or polynucleotides to identify those progeny that comprise a nucleic acid sequence encoding RAG. Also, MAB can be used to confirm the results obtained from the quantitative bioassays. In some embodiments, the markers defined herein are suitable to select proper offspring plants by genotypic screening.

Following screening, the F1 hybrid plants that exhibit an *Aphis glycines* resistant phenotype or, in some embodiments, genotype and thus comprise the requisite nucleic acid sequence encoding RAG, are then selected and backcrossed to the recurrent parent or selfed for a number of generations in order to allow for the soybean plant to become increasingly homozygous. This process can be performed for two, three, four, five, six, seven, eight, or more generations. In principle, the progeny resulting from the process of crossing the recurrent parent with the *Aphis glycines* resistant non-recurrent parent are homozygous for one or more genes that encode RAG.

In general, a method of introducing a desired trait into a soybean variety can comprise:

(a) crossing an soybean parent with another soybean plant that comprises one or more desired traits, to produce F1 progeny plants, wherein the desired trait is RAG;

(b) selecting the F1 progeny plants that have the desired trait to produce selected F1 progeny plants, in some embodiments using molecular markers as defined herein;

(c) backcrossing the selected progeny plants with the soybean parent plant to produce backcross progeny plants;

(d) selecting for backcross progeny plants that have the desired trait and morphological and physiological characteristics of the soybean parent plant, wherein the selection comprises the isolation of genomic DNA, and testing the DNA for the presence of at least one molecular marker for RAG, in some embodiments as described herein;

(e) repeating steps (c) and (d) two or more times in succession to produce selected third or higher backcross progeny plants;

(f) optionally selfing selected backcross progeny in order to identify homozygous plants; and (g) crossing at least one of the backcross progeny or selfed plants with another soybean parent plant to generate a hybrid soybean variety with the desired trait and all of the morphological and physiological characteristics of hybrid soybean variety when grown in the same environmental conditions.

As indicated, the last backcross generation can be selfed in order to provide for homozygous pure breeding (inbred) progeny for RAG. Thus, the result of recurrent selection, backcrossing, and selfing is the production of lines that are genetically homogenous for the genes associated with RAG, and in some embodiments as well as for other genes associated with traits of commercial interest.

VII. *Aphis glycines* Resistant Soybean Plants and Seeds

The goal of plant breeding is to combine in a single variety or hybrid various desirable traits. For commercial crops, these traits can include resistance to diseases and insects, tolerance to heat and drought, reducing the time to crop maturity, greater yield, and better agronomic quality. Uniformity of plant characteristics such as germination and stand establishment, growth rate, maturity, and plant height can also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid soybean variety in a soybean plant breeding program can, in some embodiments, involve three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding, successive filial generations will merely serve to increase seed of the developed inbred. In some embodiments, an inbred line comprises homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid soybean plants can then be generated from this hybrid seed supply.

An *Aphis glycines* resistant soybean plant, or a part thereof, obtainable by a method of the presently disclosed subject matter is an aspect of the presently disclosed subject matter.

Another aspect of the presently disclosed subject matter relates to an *Aphis glycines* resistant soybean plant, or part thereof, comprising the disclosed RAG loci in any configuration as described in detail above wherein at least one of the disclosed RAG loci is not in its natural genetic background. The *Aphis glycines* resistant soybean plants of the presently disclosed subject matter can be heterozygous or homozygous for the resistance traits (in some embodiments, homozygous). Although the RAG loci of the presently disclosed subject matter, as well as resistance-conferring parts thereof, can be transferred to any plant in order to provide for an *Aphis glycines* resistant plant, the methods and plants of the presently disclosed subject matter are in some embodiments related to plants of the genus *Glycine*.

The *Aphis glycines* resistant soybean lines described herein can be used in additional crossings to create *Aphis glycines* resistant plants. For example, a first *Aphis glycines* resistant soybean plant of the presently disclosed subject matter can be crossed with a second soybean plant possessing commercially desirable traits such as, but not limited to, disease resistance, insect resistance, desirable nutritional characteristics, and the like. In some embodiments, this second soybean line is itself *Aphis glycines* resistant. In some embodiments, this line is heterozygous or homozygous for one or more of the disclosed RAG loci, in order for one or more of these traits to be expressed in the hybrid offspring plants.

Another aspect of the presently disclosed subject matter relates to a method of producing seeds that can be grown into *Aphis glycines* resistant soybean plants. In some embodiments, the method comprises providing an *Aphis glycines* resistant soybean plant of the presently disclosed subject matter, crossing the *Aphis glycines* resistant plant with another soybean plant, and collecting seeds resulting from the cross, which when planted, produce *Aphis glycines* resistant soybean plants.

In some embodiments, the method comprises providing an *Aphis glycines* resistant soybean plant of the presently disclosed subject matter, crossing the *Aphis glycines* resistant plant with a soybean plant, collecting seeds resulting from the cross, regenerating the seeds into plants, selecting *Aphis glycines* resistant plants by any of the methods described herein, self-pollinating the selected plants for a sufficient number of generations to obtain plants that are fixed for an allele associated with *Aphis glycines* resistance in the plants, backcrossing the plants thus produced with soybean plants having desirable phenotypic traits for a sufficient number of generations to obtain soybean plants that are *Aphis glycines* resistant and have desirable phenotypic traits, and collecting the seeds produced from the plants resulting from the last backcross, which when planted, produce soybean plants which are *Aphis glycines* resistant.

VIII. Other Applications

With the use of these SNPs for breeding new soybean lines, a system for developing germplasm that has more than one mode of action against aphids is made possible. The use of multiple modes of action will assist in inhibiting the aphids from developing resistance. Additionally, a regime for inhibiting resistance in aphids can include a number of different modes of action. The different modes of action in an inhibiting resistance in aphids method could involve germplasm or seed treatments or chemical applications. A system for inhibiting resistance in aphids includes germplasm with one or more vertical resistant traits, and/or germplasm with one or more horizontal tolerance traits with the possible options of including a seed treatment that is active against the aphids, and/or an insecticidal spray. Insecticidal sprays or treatments can include known insecticidal or insect-deterring compounds for aphids or other insects.

The regime for inhibiting resistance in aphids plays a role in the continued effectiveness of germplasm resistance and chemical activity. There are geographic areas where soybeans are presently produced that have aphids that are not negatively affected by the Rag1 resistant allele (Kim et al., 2008; Mian et al. 2008a, 2008b; Kang et al. 2008). The ability of this insect to evolve so quickly could render entire soybean growing areas unprofitable; unless the embodiments of the presently disclosed subject matter that provide soybean seeds which are protected by the SNP selected traits for a dual mode of action plus the optional seed treatment, or chemical applications, are implemented.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

SNP Analysis

There are SSR markers that are associated with the resistant gene Rag1 This SSR information was employed to identify SNP markers that map to the region of qualitative genes and quantitative trait loci (QTL) defined for the Rag1 gene. The identified SNPs were validated on *Aphis glycines* resistant and susceptible lines. Analyses indicated that these SNPs showed better associations to the Rag1 gene than did the SSRs. The information of validated SNPs for RAG is new and is used for appropriate breeding programs.

Example 2

SNP Genotyping Data

Molecular markers were identified for the Rag1 gene. Li et al., 2007 used Dowling lines to map Rag1 to linkage group (LG) M between the SSR markers Satt435 and either Satt463 or Satt245. The approximate positions of these genes and various markers are depicted in FIG. 1.

The soybean linkage map developed by scientists at the USDA and made publicly available in 2006 can be found at http://bfgl.anri.barc.usda.gov/soybean and is discussed in Choi et al., 2007. This map was used to locate the flanking SSRs associated with Rag1 and to select SNPs that were mapped within and close to each region. The polymorphism information and genomic sequence on either side of the SNP was used to design PCR-based assays to detect each allele. The sequences with the SNP indicated were either submitted to the Applied Biosystems Inc. (ABI; Foster City, Calif., United States of America) Assay-by-Design service for creation of custom TAQMAN® (Applied Biosystems Inc., Foster City, Calif., United States of America) based assays, or assays were manually designed using the ABI software PRIMER EXPRESS®. Similarly, TAQMAN® assays can be designed using software available from Biosearch Technologies (Novato, Calif., United States of America).

A goal of the SNP assay was to be able to determine which polymorphism(s), or allele(s), is/are present in the genome of any given soybean line, and ultimately to permit the selection of preferred allele(s) (i.e., *Aphis glycines* resistant gene(s)), in a marker-assisted breeding program. A total of 3 SNPs were identified. Screening panel DNAs isolated from resistant lines (Dowling) were used for the assays.

Example 3

Allelic Discrimination Assays

In allelic discrimination assays, a PCR assay included a forward and reverse primer and a specific, fluorescent, dye-labeled probe for each of two alleles for a given SNP. The probes contained different fluorescent reporter dyes (VIC®; Applied Biosystems, Inc., Foster City, Calif., United States of America; and 6-carboxyfluorescein-aminohexyl amidite (FAM), or N-TET-6-Aminohexanol (TET) and FAM) to differentiate the amplification of each allele. A non-fluorescent quencher on each probe suppressed the fluorescence until amplification by PCR. During PCR, each probe annealed specifically to complementary sequences between the forward and reverse primer sites. Taq polymerase then cleaved the probes that were hybridized to each allele. Cleavage separated the reporter dye from the quencher, which resulted in increased fluorescence by the reporter dye.

Thus, the fluorescent signals generated by PCR amplification indicated that one or both alleles were present in the sample. Probes are designed with higher Tm than the primers. These probes therefore exhibited greater Tm differences when hybridized to matched and mismatched templates, which provided more accurate allelic discriminations. Probes of this type were manufactured at either ABI (MGB™ quencher) or Biosearch Technologies (BHQPLUS™ quencher). At the end of PCR thermal cycling, fluorescence of the two reporter dyes was measured on an ABI 7900. An increase in fluorescence for one dye only indicated homozygosity for the corresponding allele. An increase in both fluorescent signals indicated heterozygosity.

Exemplary starting lines and haplotypes determined using this method are presented in Tables 3-4.

TABLE 3

SNP Screening Panel

| Line | Name | Origin | Resistance |
|---|---|---|---|
| PI548663 | Dowling | US | Rag1 |
| PI606749 | Ina | US | susceptible |
| PI614088 | Loda | US | susceptible |

TABLE 4

SNP Genotyping Data - Detailed for Rag1

| Line | Name | LOCUS | SEQ ID NO: 1 A 38.048 Rag1 | SEQ ID NO: 2 C 39.1 Rag1 | SEQ ID NO: 3 A 47.4 Rag1 |
|---|---|---|---|---|---|
| PI548663 | Dowling | Rag1 | A | C | A |
| PI606749 | Ina | Susceptible | T | G | G |
| PI614088 | Loda | Susceptible | T | G | G |

Example 4

TAQMAN® Validation

To validate TAQMAN® allelic discrimination assays for association with insect resistance or tolerance, plants were selected based on their known phenotypic status and compared to the genotype at the specific SNP location. DNA was extracted from leaf tissue of seedlings 7-10 days after planting. DNA can be extracted from plant tissue in a variety of ways, including the CTAB method, sodium hydroxide, and the Dellaporta method (Dellaporta et al., 1983). DNA is diluted in TE buffer and stored at 4° C. until used in PCR reactions as described below.

PCR was set up in 5 µl final volumes according to the following formula:

| Reagent | Stock concentration | Per rxn (µl) | Final concentration |
|---|---|---|---|
| 2X Master Mix* | 2X | 2.5 | 1X |
| AbD primer/probe mix (80x) | 40x | .0625 | 0.5x |
| PCR-quality H2O | — | 2.44 | — |
| DNA (dried in 384) | 4.5 ng/µl | 4 | 3.6 ng/µl (18 ng) |
| Final Volume (µl) | | 5.00 | |

*The Master Mix is JUMPSTART ™ Taq READYMIX ™ (Sigma Catalogue No. 2893; Sigma Chemical Co., St. Louis, Missouri, United States of America), a premix of all the components, including nucleotides and Taq polymerase (but not primers and/or probes) necessary to perform a 5'-nuclease assay. Before use, 1375 µl of 1.0 M MgCl₂ (Sigma Catalogue No. M1028) and 250 µl of 300 µM Sulforhodamine 101(Sigma Catalogue No. S7635), (Sigma Catalogue No. S7635), also known as ROX, are added to a 125 mL bottle of JUMPSTART ™ Taq READYMIX ™.

PCR plates were placed in an ABI 9700 thermal cycler and the following program was run:

| Task | Snp1 |
|---|---|
| Initial denaturation | 50° C. for 2 min; followed by 95° C. for 10 min |
| Cycles | 95° C. for 15 sec; 60° C. for 1 min |
| Number of cycles | 40 |
| Final elongation | 72° C. for 5 min |
| Hold at 4° C. | |

The ABI 7900 Sequence Detection System (or TAQMAN®) was used to visualize the results of an allelic discrimination (SNP) assay. Using the Sequence Detection System (SDS) software, allele calls were made based on the fluorescence for the 2 dyes measured in each sample.

Example 5

KASPar Assay Validation

Summary of PCR-Based Genotyping Assay

In some embodiments, PCR-based assays are employed that use amplification primers that differ in their 3'-terminal nucleotides in order to distinguish between alleles. In these embodiments, amplification reactions can be designed in which a single primer on one "side" of an SNP (arbitrarily defined as the "reverse" primer) can be paired with two different "forward" primers that differ only in their 3' most nucleotide. One such forward primer can be designed to bind to one of the alleles of the SNP, and the other such forward primer can be designed to bind to the other of the alleles of the SNP, with the 3' most nucleotide designed to hybridize at the SNP position itself.

For example, SEQ ID NO: 19 is a nucleotide sequence from the Rag1 locus that contains SNPs at nucleotides 33 (A/G) (A being desirable), 78 (G/T) (T being desirable), 104 (C/T), (T being desirable) and 208 (NC) (A being desirable). With respect to genotyping plants to identify which of the alleles for the SNP at nucleotide 33 of SEQ ID NO: 19 are present, a pair of PCR reactions can be done in which one reaction includes oligonucleotides that comprise (in some embodiments, consist of) SEQ ID NO: 20 and SEQ ID NO: 28 and the other reaction includes oligonucleotides that comprise (in some embodiments, consist of) SEQ ID NO: 21 and SEQ ID NO: 28. SEQ ID NOs: 20 and 21 are essentially identical to each other with the exception of the 3'-most nucleotide, which in the case of SEQ ID NO: 20 is an A and in the case of SEQ ID NO: 21 is a G. If the "A allele" is present, the PCR reaction employing SEQ ID NOs: 20 and 28 will yield an amplification product. If the "G allele" is present, the PCR reaction employing SEQ ID NOs: 21 and 28 will yield an amplification product.

SEQ ID NOs: 20 and 21 also differ at their 5' ends, with SEQ ID NO: 20 (and, for that matter, SEQ ID NOs: 22, 24, and 26) having a 5' tag (i.e., SEQ ID NO: 32) and SEQ ID NO: 21 (and, for that matter, SEQ ID NOs: 23, 25, and 27) having a different 5' tag (i.e., SEQ ID NO: 32). It is understood that these tags can be deleted or modified without affecting the use of the corresponding oligonucleotides in the instant PCT-based assays. The locations of the subsequences to which primers comprising SEQ ID NOs: 20-31 would be expected to hybridize to SEQ ID NO: 19 are provided in FIGS. 3A-3D.

It is understood that in order to use the instant strategy for differentially genotyping plants to identify the presence of one or more of the alleles at nucleotide 33 of SEQ ID NO: 19, it is preferable that the oligonucleotides employed do not include any nucleotides added to at the 3' ends of SEQ ID NOs: 20 and 21. As such, in some embodiments the oligonucleotides employed in conjunction with SEQ ID NO: 28 consist of SEQ ID NOs: 20 and 21 (optionally with one or both of 5' tags SEQ ID NO: 32 and SEQ ID NO: 33 deleted).

Similar strategies for genotyping alleles with respect to the SNPs at nucleotides 78, 104, and 208 of SEQ ID NO: 19 can be performed using oligonucleotides that comprise (in some embodiments, consist of) SEQ ID NO: 22 or SEQ ID NO: 23 in conjunction with SEQ ID NO: 29, SEQ ID NO: 24 or SEQ ID NO: 25 in conjunction with SEQ ID NO: 30, and SEQ ID NO: 26 or SEQ ID NO: 27 in conjunction with SEQ ID NO: 31, respectively. In some embodiments, the 5' tags present in SEQ ID NOs: 22-27 are not present in the oligonucleotides employed for analysis.

KASPar assays employ PCR with two allele specific primers (one specific to each nucleotide of the SNP), and one common primer in the opposite orientation. Fluorescent signals (FAM and/or VIC®) are generated by Kbioscience proprietary master mix during PCR. The unlabeled primers can be ordered from any oligonucleotide vendor.

A the end of PCR thermal cycling, fluorescence of the two reporter dyes is measured with a fluorescence plate reader or real-time PCR machine compatible with FAM, VIC and ROX (e.g., ABI TaqMan 7900). An increase in fluorescence for FAM or VIC only indicated homozygosity for the corresponding allele. An increase in both fluorescent signals indicated heterozygosity.

Exemplary starting lines and haplotypes determined using this method are presented below.

| Line | Name | Origin | Resistance |
|---|---|---|---|
| PI548663 | Dowling | US | Rag1 |
| PI597386 | Dwight | US | Susceptible |
| MT9131044 | | US | Susceptible |

| Line | Name | Locus | SEQ ID No 19 at 33 | SEQ ID No 19 at 78 | SEQ ID No 19 at 104 | SEQ ID No 19 at 208 |
|---|---|---|---|---|---|---|
| PI548663 | Dowling | Rag1 | A | T | T | A |
| PI597386 | Dwight | Susceptible | G | G | C | C |
| MT9131044 | | Susceptible | G | G | C | C |

Example 6

KASPar Validation

To validate KASPar allele specific PCR assays for association with insect resistance or tolerance, plants were selected based on their known phenotypic status and compared to the genotype at the specific SNP location. DNA was extracted from leaf tissue of seedlings 7-10 days after planting. DNA can be extracted from plant tissue in a variety of ways, including the CTAB method, sodium hydroxide, and the Dellaporta method (Dellaporta et al., 1983). DNA is diluted in TE buffer and stored at 4° C. until used in PCR reactions as described below.

PCR was set up in 4 ul final volumes according to the following formula:

| Reagent | Stock concentration | Per rxn (ul) | Final concentration |
|---|---|---|---|
| Genomic template DNA | 5-50 ng/ul | 2 | 10-100 ng |
| KASPar master mix | 4X | 1 | 1X |
| Primer mix* | See below | 0.55 | See below |
| Taq polymerase | | 0.013 | |
| MgCl2 | 50 mM | 0.32 | 4 mM |
| H2O | — | 0.9 | — |

*12 uM each allele-specific primer and 30 uM common primer The KASPar master mix (KBioscience) contains a premix of all the components necessary for the reaction including nucleotides and reporter dyes (FAM and VIC). MgCl2 is added separately and the concentration can be adjusted per GC content of a particular assay. Taq polymerase is added just before thermal cycling.

PCR plates are placed in a thermal cycler and the following program is run:

| Task | Temperature |
|---|---|
| Initial denaturation | 94° C. for 15 minutes |
| Cycles | 94° C. for 10 seconds, 57° C. for 5 seconds, 72° C. for 10 seconds |
| Number of cycles | 20 |
| Cycles | of 94° C. for 10 seconds, 57° C. for 20 seconds, 72° C. for 40 seconds |
| Number of cycles | 18 |
| Final elongation | 72° C. for 5 minutes |
| Hold at 4° C. | |

The ABI 7900 Sequence Detection System (or TAQ-MAN®) or another fluorescence plate reader or real-time PCR machine compatible with FAM, VIC and ROX was used to visualize the results of an allelic specific PCR (SNP) assay.

Using the Sequence Detection System (SDS) software, allele calls were made based on the fluorescence for the 2 dyes measured in each sample.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent not inconsistent herewith and to the extent that they supplement, explain, provide a background for, or teach methodology, techniques, and/or compositions employed herein.

Gomez et al. (2006) Environ Exp Bot 55:77-86.

Hartman et al. (2001) Occurrence and distribution of *Aphis glycines* on soybeans in Illinois in 2000 and its potential control. [Online]. [3 p.] Available at http://www.plantmanagementnetwork.org/php/default.asp (accessed Mar. 19, 2009).

Hill et al. (2004) Crop Science 44: 98

Hill et al. (2006) Crop Science 46: 1601

Kang et al. (2008) Crop Sc 48:1744-1748.
Kim et al. (2008) Crop Sc 48:923-928.
Landis et al. NCR-125 Arthropod biological control: state reports for 2003.
Li et al. (2007) Mol Breeding 19:25-34.
Mian et al. (2008a) Crop Sci 48:1055-1061.
Mian et al. (2008b) Theor Appl Genet. 117:955-962.
PCT International Patent Application Publication Nos. WO 2006/125065; WO 2006/002162; and WO 2008/067043.
U.S. patent application Ser. No. 11/158,307, published as U.S. Patent Application Publication No. 2006/0015964.
Wang et al. (2006) Plant Dis 90:920-926.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for selecting a soybean plant with resistance to *Aphis glycines* (RAG), the method comprising:
   (a) genotyping one or more soybean plants with respect to one or more single nucleotide polymorphisms (SNPs), wherein the one or more SNPs correspond to one or more molecular markers selected from the group consisting of an A at nucleotide 203 of SEQ ID NO: 1, an A at position 615 of SEQ ID NO: 3, an A at position 33 of SEQ ID NO: 19, a T at position 78 of SEQ ID NO: 19, a T at position 104 of SEQ ID NO: 19, and an A at position 208 of SEQ ID NO: 19; and
   (b) selecting a soybean plant that includes at least one resistance allele associated with the SNPs, thereby selecting an *Aphis glycines* resistant soybean plant.

2. A method for selecting a soybean plant with resistance to *Aphis glycines* (RAG), the method comprising:
   (a) isolating one or more nucleic acids from a plurality of soybean plants;
   (b) detecting in said isolated nucleic acids the presence of one or more single nucleotide polymorphisms (SNPs) corresponding to one or more marker molecules associated with RAG, wherein said marker molecule is selected from the group consisting of an A at nucleotide 203 of SEQ ID NO: 1, an A at position 615 of SEQ ID NO: 3, an A at position 33 of SEQ ID NO: 19, a T at position 78 of SEQ ID NO: 19, a T at position 104 of SEQ ID NO: 19, and an A at position 208 of SEQ ID NO: 19; and
   (c) selecting a soybean plant comprising said one or more marker molecules, thereby selecting an *Aphis glycines* resistant soybean plant.

3. The method of claim 2, wherein said one or more marker molecules comprises an A at nucleotide 203 of SEQ ID NO: 1; and/or an A at position 615 of SEQ ID NO: 3; an A at position 33 of SEQ ID NO: 19; a T at position 78 of SEQ ID NO: 19; a T at position 104 of SEQ ID NO: 19; or an A at position 208 of SEQ ID NO: 19.

4. The method of claim 2, further comprising:
   (d) selecting a first donor parental line from step (c) possessing a desired *Aphis glycines* resistance and having at least one of the marker molecules mapped by one or more of the markers: an A at nucleotide 203 of SEQ ID NO: 1, an A at position 615 of SEQ ID NO: 3, an A at position 33 of SEQ ID NO: 19, a T at position 78 of SEQ ID NO: 19, a T at position 104 of SEQ ID NO: 19, and/or an A at position 208 of SEQ ID NO: 19;

(e) crossing the first donor parental line with a second parental line in hybrid combination to produce a segregating plant population; and (f) screening the segregating population for resistant loci of one or more genes associated with the RAG.

5. The method of claim 4, further comprising:

(g) selecting plants from the population having the resistant loci for further screening until a line is obtained which is homozygous for RAG at sufficient loci to give RAG in hybrid combination.

6. The method of claim 4, further comprising:

screening an introgressed soybean from step (f) for RAG.

7. The method of claim 5, further comprising:

screening an introgressed soybean from step (g) for RAG.

* * * * *

SEQUENCE LISTING

```
<160> NUMBER OF SEQ ID NOS: 33

<210> SEQ ID NO 1
<211> LENGTH: 498
<212> TYPE: DNA
<213> ORGANISM: Glycine max
<220> FEATURE:
<221> NAME/KEY: misc_feature
<222> LOCATION: (1)..(498)
<223> OTHER INFORMATION: k is g or t; m is a or c; r is a or g; w is a
      or t; and y is c or t

<400> SEQUENCE: 1
ttcctttact tttggctgat cgctcatatg ggagtgaaag agaatagaat atattaccat        60
attgaaaagg tatgtccttc ccttgtgttt ggacaactta ctatttarca acgaacaaaa       120
cttacataca aatctttagg ctccttataa ccttgttatt tgatcaaaat taaagtttya       180
tttcaataat ctacataata gawgtttaca tgtagattat cgagataaac ttcaattttg       240
gtcgaaaata aacaccaaat atacttataa aattacatct aagttttatc cttcaacaaa       300
tgacacargc attgggattc tcttccatgc ttggagcata gtagtktgtg gtcatgtagg       360
grttatatgc cctataagcc ttgaccmatt ccaaaacagg atctggggct ggctcttttct      420 tcttatcatc ctccttcttc tcttcttttct ttccttcttc cttctttccc tcctctttct     480
tttctccctc cttctttg                                                    498

<210> SEQ ID NO 2
<211> LENGTH: 367
<212> TYPE: DNA
<213> ORGANISM: Glycine max
<220> FEATURE:
<221> NAME/KEY: misc_feature
<222> LOCATION: (191)..(191)
<223> OTHER INFORMATION: s is c or g

<400> SEQUENCE: 2
attcattcac taattgatta ttagccttag aaattcaaat gatataatct gaccactcag        60
agataaagga agtatggtcc atggactccc caggaacatc ctcgtgctta gagggcttct       120
ccttcccacc aaccaacctg gctgggttcc caacagctgt tgtctgtggt ggcacatcga       180
ttaaaaccac sgagccagca ccaacctttg caccttcccc gatcttaata ttccccagaa       240
tggtagcacc ggcaccaata agcaccccat ccccaatctt gggatgccgg tccccaccaa       300
ccttgccagt cccacccagc gtaacgtggt gcaggatcga cacattgttc ccgatcactg       360
gccccgt                                                                367

<210> SEQ ID NO 3
<211> LENGTH: 1057
<212> TYPE: DNA
<213> ORGANISM: Glycine max
<220> FEATURE:
<221> NAME/KEY: misc_feature
```

<222> LOCATION: (1)..(1057)
<223> OTHER INFORMATION: k is g or t; r is a or g; w is a or t; and y is
      c or t

<400> SEQUENCE: 3
agttgaagca gaacagtgta aatggaaacg gcagcacttt aagagggttt acatgtaacc      60
agaagcattg ycttaaaaat taaktgcagt aaaggtttga atccattcac ctgggtttaa     120
atgctaaaaa taaggtatat ttgcagtgta tctakggaga gtctactcca aactaggtgc     180
tacctctgtt ggattggaat caaaaacatc tgagtcatat gyatcaggct cttcaataac     240
tttaccggac tccacactgg aatctgcact agactccaaa ccggactctg cactagactc     300
cacgccggac tgcacagaat acagcctttc agcagcctcc ctcatttctt ttggtggttc     360
atgaaatgta aagcaaccgt agatagcaag acatgcctac aatcccagtg aacataaaca     420
cgtttaaagc cttgattgaa tcaacgtgta aattgcgaga ctagactaca ctcaaaattt     480
ccagacaaga ctccgcactg ttytcctagt wcccactttg tgagaactaa ccccatttcc     540
attaactttt tttctttctt tcaaaaaata aaacaaagaa ggcttcaaaa ttttgtaaat     600
aaattaagag tctcrtcctg tgtatggaat aacatcaatt agaagagctc aatcacctaa     660
acaaatctca ttacattgag atattagtgt ttgactcgat accaccccag aaaaataagg     720
cctgattttt tctgctaaac gtacaccccct taattacaga aatgtttata tcagagcagt     780
catgcagcaa acgccaggag caaccgacct gtgcacaaac tagagtaaac acacatcttt     840
tagattaaat ttagacatat cgtttcccct ctctatcaag cttcattcac agctgaatgt     900
tactactgga ccaatcggct aaccatctta atgactgatt cgcattactg taccatgtca     960
gacgtgctat aactactagc ctactctttc actatgagag atcgctcaat cgggtctgaa    1020
taatttagtg atgctactct tgaaacaagg caacctc                             1057

<210> SEQ ID NO 4
<211> LENGTH: 33
<212> TYPE: DNA
<213> ORGANISM: Glycine max

<400> SEQUENCE: 4
cttacataca aatctttagg ctccttataa cct      33

<210> SEQ ID NO 5
<211> LENGTH: 30
<212> TYPE: DNA
<213> ORGANISM: Glycine max

<400> SEQUENCE: 5
tggtgtttat tttcgaccaa aattgaagtt      30

<210> SEQ ID NO 6
<211> LENGTH: 18
<212> TYPE: DNA
<213> ORGANISM: Glycine max

<400> SEQUENCE: 6
tggctgggtt cccaacag      18

<210> SEQ ID NO 7
<211> LENGTH: 20
<212> TYPE: DNA
<213> ORGANISM: Glycine max

<400> SEQUENCE: 7
gggaaggtgc aaaggttggt                                                     20

<210> SEQ ID NO 8
<211> LENGTH: 33
<212> TYPE: DNA
<213> ORGANISM: Glycine max

<400> SEQUENCE: 8
cccatttcca ttaactttt ttctttcttt caa                                      33

<210> SEQ ID NO 9
<211> LENGTH: 29
<212> TYPE: DNA
<213> ORGANISM: Glycine max

<400> SEQUENCE: 9
tgagatttgt ttaggtgatt gagctcttc                                           29

<210> SEQ ID NO 10
<211> LENGTH: 24
<212> TYPE: DNA
<213> ORGANISM: Glycine max
<220> FEATURE:
<221> NAME/KEY: misc_feature
<222> LOCATION: (1)..(24)
<223> OTHER INFORMATION: This oligonucleotide can optionally be labeled
      with VIC

<400> SEQUENCE: 10
atctacatgt aaacttctat tatg                                                24

<210> SEQ ID NO 11
<211> LENGTH: 15
<212> TYPE: DNA
<213> ORGANISM: Glycine max
<220> FEATURE:
<221> NAME/KEY: misc_feature
<222> LOCATION: (1)..(15)
<223> OTHER INFORMATION: This oligonucleotide can optionally be labeled
      with VIC

<400> SEQUENCE: 11
ctggctcggt ggttt                                                          15

<210> SEQ ID NO 12
<211> LENGTH: 24
<212> TYPE: DNA
<213> ORGANISM: Glycine max
<220> FEATURE:
<221> NAME/KEY: misc_feature
<222> LOCATION: (1)..(24)
<223> OTHER INFORMATION: This oligonucleotide can optionally be labeled
      with VIC

<400> SEQUENCE: 12
ataaattaag agtctcatcc tgtg                                                24

<210> SEQ ID NO 13
<211> LENGTH: 22
<212> TYPE: DNA
<213> ORGANISM: Glycine max
<220> FEATURE:
<221> NAME/KEY: misc_feature
<222> LOCATION: (1)..(22)
<223> OTHER INFORMATION: This oligonucleotide can optionally be labeled
      with FAM

<400> SEQUENCE: 13

```
ctacatgtaa acatctatta tg                                             22
```

```
<210> SEQ ID NO 14
<211> LENGTH: 15
<212> TYPE: DNA
<213> ORGANISM: Glycine max
<220> FEATURE:
<221> NAME/KEY: misc_feature
<222> LOCATION: (1)..(15)
<223> OTHER INFORMATION: This oligonucleotide can optionally be labeled
      with FAM

<400> SEQUENCE: 14
ctggctccgt ggttt                                                     15

<210> SEQ ID NO 15
<211> LENGTH: 20
<212> TYPE: DNA
<213> ORGANISM: Glycine max
<220> FEATURE:
<221> NAME/KEY: misc_feature
<222> LOCATION: (1)..(20)
<223> OTHER INFORMATION: This oligonucleotide can optionally be labeled
      with FAM

<400> SEQUENCE: 15
attaagagtc tcgtcctgtg                                                20

<210> SEQ ID NO 16
<211> LENGTH: 400
<212> TYPE: DNA
<213> ORGANISM: Glycine max

<400> SEQUENCE: 16
ttcctttact tttggctgat cgctcatatg ggagtgaaag agaatagaat atattaccat     60
attgaaaagg tatgtccttc cctttgtgttt ggacaactta ctatttagca acgaacaaaa   120
cttacataca aatctttagg ctccttataa ccttgttatt tgatcaaaat taaagttttta  180 tttcaataat ctacataata gaagtttaca tgtagattat cgagataaac ttcaattttg    240
gtcgaaaata aacaccaaat atacttacaa aattacatct aagttttatc cttcaacaaa    300
tgacacaagc attgggattc tcttccatgc ttggagcata gtagtttgtg gtcatgtagg    360
ggttatatgc cctataagcc ttgacccatt ccaaaacagg                          400

<210> SEQ ID NO 17
<211> LENGTH: 357
<212> TYPE: DNA
<213> ORGANISM: Glycine max

<400> SEQUENCE: 17
cagtgatcgg gaacaatgtg tcgatcctgc accacgttac gctgggtggg actggcaagg     60
ttggtgggga ccggcatccc aagattgggg atgggtgct tattggtgcc ggtgctacca     120 ttctgggaa tattaagatc ggggaaggtg caaaggttgg tgctggctcg gtggttttaa    180
tcgatgtgcc accacagaca acagctgttg ggaacccagc caggttggtt ggtgggaagg    240
agaagccctc taagcacgag gatgttcctg gggagtccat ggaccatact tccttttatct   300 ctgagtggtc agattatatc atttgaattt ctaaggctaa tcaattagtg aatgaat        357

<210> SEQ ID NO 18
<211> LENGTH: 703
<212> TYPE: DNA
<213> ORGANISM: Glycine max
```

-continued

```
<400> SEQUENCE: 18
cactttaaga gggtttacat gtaaccagaa gcattgtctt aaaaattaag tgcagtaaag      60
gtttgaatcc attcacctgg gtttaaatgc taaaaataag gtatatttgc agtgtatcta    120
tggagagtct actccaaact aggtgctacc tctgttggat tggaatcaaa acatctgag     180 tcatatgtat caggctcttc ataacttta ccggactcca cactggaatc tgcactagac    240
tccaaaccgg actctgcact agactccacg ccggactgca cagaatacag cctttcagca    300
gcctccctca tttcttttgg tggttcatga aatgtaaagc aaccgtagat agcaagacat    360
gcctacaatc ccagtgaaca taaacacgtt taaagccttg attgaatcaa cgtgtaaatt    420
gcgactagac tacactcaaa atttccagac aagactccgc actgttttcc tagttccact    480
ttgtgagaac taaccccatt tccattaact ttttttcttt ctttcaaaaa ataaaacaaa    540
gaaggcttca aaattttgta aataaattaa gagtctcgtc ctgtgtatgg aataacatca    600
attagaagag ctcaatcacc taaacaaatc tcattacatt gagatattag tgtttgactc    660
gataccaccc agaaaaaatt aaggcctgat tttttctgct aaa                      703

<210> SEQ ID NO 19
<211> LENGTH: 583
<212> TYPE: DNA
<213> ORGANISM: Glycine max
<220> FEATURE:
<221> NAME/KEY: misc_feature
<222> LOCATION: (1)..(583)
<223> OTHER INFORMATION: k is g or t; m is a or c; r is a or g; and y is
      c or t

<400> SEQUENCE: 19
ccagtatcac aaacaagtca tgggtgacca aarcaattgg agattttccc atgtgttgtc      60
ttcaacatga aactgtgkag gctaacaact tatcctcatt tatytgcagg atctgaatat    120
ttaagactag cgacacacag aggatataac cagggcaggt aaattttccc aataaataca    180
accccctaga gtgatggatc caagaatmtt tccaatggac atatcaacat tacaatccct    240
caaaatccat atcattacag acatgcctcc caatgagagt ctgaatacta ctcctttgca    300
tcgttatact gccacttttc acatatcaga cacagaccaa agataagctt ctctatctct    360
agcttgcttc tcatttgttc tcttgaacat atccttttcg aaccctacaa acagcagaag    420
ataagtcaat catttaagac tatttccatg agaaaagtca aggtaaaatc aaagcacaaa    480
aaagtatggc gaatatgaac ccaccattac tacgatcaac accatcccag tgtcgtccag    540
gccttattcc atatcgattt ggagcagcgt ctaaactccg ttt                      583

<210> SEQ ID NO 20
<211> LENGTH: 47
<212> TYPE: DNA
<213> ORGANISM: Glycine max

<400> SEQUENCE: 20
gaaggtgacc aagttcatgc tcacaaacaa gtcatgggtg accaaaa                   47

<210> SEQ ID NO 21
<211> LENGTH: 46
<212> TYPE: DNA
<213> ORGANISM: Glycine max

<400> SEQUENCE: 21
gaaggtcgga gtcaacggat tacaaacaag tcatgggtga ccaaag                    46
```

<210> SEQ ID NO 22
<211> LENGTH: 47
<212> TYPE: DNA
<213> ORGANISM: Glycine max

<400> SEQUENCE: 22
gaaggtgacc aagttcatgc tgtgttgtct tcaacatgaa actgtgg           47

<210> SEQ ID NO 23
<211> LENGTH: 47
<212> TYPE: DNA
<213> ORGANISM: Glycine max

<400> SEQUENCE: 23
gaaggtcgga gtcaacggat tgtgttgtct tcaacatgaa actgtgt           47

<210> SEQ ID NO 24
<211> LENGTH: 46
<212> TYPE: DNA
<213> ORGANISM: Glycine max

<400> SEQUENCE: 24
gaaggtgacc aagttcatgc tagtcttaaa tattcagatc ctgcag            46

<210> SEQ ID NO 25
<211> LENGTH: 49
<212> TYPE: DNA
<213> ORGANISM: Glycine max

<400> SEQUENCE: 25
gaaggtcgga gtcaacggat tgctagtctt aaatattcag atcctgcaa         49

<210> SEQ ID NO 26
<211> LENGTH: 46
<212> TYPE: DNA
<213> ORGANISM: Glycine max

<400> SEQUENCE: 26
gaaggtgacc aagttcatgc tccctagagt gatggatcca agaata           46

<210> SEQ ID NO 27
<211> LENGTH: 45
<212> TYPE: DNA
<213> ORGANISM: Glycine max

<400> SEQUENCE: 27
gaaggtcgga gtcaacggat tcctagagtg atggatccaa gaatc            45

<210> SEQ ID NO 28
<211> LENGTH: 29
<212> TYPE: DNA
<213> ORGANISM: Glycine max

<400> SEQUENCE: 28
gaagacaaca catgggaaaa tctccaatt                              29

<210> SEQ ID NO 29
<211> LENGTH: 30
<212> TYPE: DNA
<213> ORGANISM: Glycine max
<220> FEATURE:
<221> NAME/KEY: misc_feature
<222> LOCATION: (10)..(10)
<223> OTHER INFORMATION: r is a or g

<400> SEQUENCE: 29

-continued

```
gatcctgcar ataaatgagg ataagttgtt                              30

<210> SEQ ID NO 30
<211> LENGTH: 27
<212> TYPE: DNA
<213> ORGANISM: Glycine max
<220> FEATURE:
<221> NAME/KEY: misc_feature
<222> LOCATION: (6)..(6)
<223> OTHER INFORMATION: k is g or t

<400> SEQUENCE: 30
ctgtgkaggc taacaactta tcctcat                                 27

<210> SEQ ID NO 31
<211> LENGTH: 30
<212> TYPE: DNA
<213> ORGANISM: Glycine max

<400> SEQUENCE: 31
ggattgtaat gttgatatgt ccattggaaa                              30

<210> SEQ ID NO 32
<211> LENGTH: 21
<212> TYPE: DNA
<213> ORGANISM: Artificial Sequence
<220> FEATURE:
<223> OTHER INFORMATION: Artificially synthesized oligonucleotide 5' tag
      A

<400> SEQUENCE: 32
gaaggtgacc aagttcatgc t                                       21

<210> SEQ ID NO 33
<211> LENGTH: 21
<212> TYPE: DNA
<213> ORGANISM: Artificial Sequence
<220> FEATURE:
<223> OTHER INFORMATION: Artificially synthesized oligonucleotide 5' tag
      B

<400> SEQUENCE: 33
gaaggtcgga gtcaacggat t                                       21
```